United States Patent [19]

Knifton et al.

[11] Patent Number: 5,171,896
[45] Date of Patent: Dec. 15, 1992

[54] ALKYLPHENOL SYNTHESIS USING ACID-MODIFIED INORGANIC CLAY CATALYSTS

[75] Inventors: John F. Knifton; Yu-Hwa E. Sheu, both of Austin, Tex.

[73] Assignee: Texaco Chemical Company, White Plains, N.Y.

[21] Appl. No.: 846,099

[22] Filed: Mar. 5, 1992

[51] Int. Cl.$^5$ .................. C07C 37/14; C07C 37/11; C07C 37/06
[52] U.S. Cl. .................. 568/791; 568/790; 568/793; 568/794
[58] Field of Search ............ 568/790, 791, 793, 794

[56] References Cited

U.S. PATENT DOCUMENTS

| | | | |
|---|---|---|---|
| 2,732,408 | 1/1956 | Foote | 568/791 |
| 2,874,193 | 2/1956 | Dijkstra | 568/791 |
| 2,975,216 | 3/1961 | Spacht | 568/781 |
| 2,975,217 | 3/1961 | Spacht | 568/791 |
| 3,211,670 | 10/1965 | Kaplan et al. | 568/791 |
| 3,992,455 | 11/1976 | Leston | 568/791 |
| 4,055,605 | 10/1977 | Jarreau | 568/791 |

*Primary Examiner*—Werren B. Lone
*Attorney, Agent, or Firm*—Jack H. Park; Kenneth R. Priem; Cynthia L. Kendrick

[57] ABSTRACT

Disclosed is a one step method for synthesis of alkylphenols which comprises reacting phenol with the corresponding olefin under adiabatic conditions in the presence of a catalyst comprising an acidic montmorillonite clay having the structure:

$$M_{x/n}{}^{n+}\cdot yH_2O(Al_{4-x}Mg_x)(Si_8)O_{20}(OH)_4$$

where M represent the interlamellar (balancing cation, normally sodium or lithium) and x, y and n are integers, wherein the acidic clay has been pretreated with an acid and optionally has deposited thereon an acid selected from the group consisting hydrogen fluoride, a fluorosulfonic acid or a mineral acid, at a temperature of from 60° C. to 250° C. and a pressure of from near atmospheric to about 500 psi.

18 Claims, No Drawings

ALKYLPHENOL SYNTHESIS USING ACID-MODIFIED INORGANIC CLAY CATALYSTS

BACKGROUND OF THE INVENTION

1. Field of the Invention

The invention relates to a one step method for the preparation of alkylphenols from phenol and the corresponding olefin. More particularly it relates to a one-step method for preparation of alkyl phenols by reacting phenols and the corresponding olefins over acid treated montmorillonite clays. The method is especially effective in the synthesis of the most desirable para-alkyl phenol, for example, para-nonylphenol, from phenol and nonene.

2. Description Of The Related Art

It is known in the art to prepare higher molecular weight alkylphenols, such as p-tert-octylphenol, p-nonylphenol and dodecylphenol by alkylating phenol with diisobutylene, propylene trimer and propylene tetramer, respectively, under acidic conditions. Nonylphenol, in particular, is used as an intermediate for surfactants, as well as antioxidants and lube oil additives.

In "Bisphenol A and Alkylated Phenols", SRI PEP Report No. 192 (Dec. 1988)., page 4—4, it is reported that it is known in the art to prepare various alkylphenols by acid catalyzed reactions of phenols with various olefins. These alkylphenols may include p-tert-butylphenol, p-isopropylphenol, p-sec-butylphenol, p-tert-octylphenol, nonylphenol and dodecylphenol. The alkylation reaction takes place at or near atmospheric pressure in the presence of an acidic catalyst such as a mineral acid, a Lewis acid (e.g. boron trifluoride) or a cation exchange resin (e.g. styrene-divinyl benzene resin). The acid catalysts lead to predominantly para-alkylated phenol when the para position is available. Generally a molar ratio of phenol to olefin of 1.5-3:1 is desired to minimize the yield of dialkylphenols.

U.S. Pat. No. 4,198,531, to BASF, discloses a process for continuous manufacture of p-alkylphenols by reacting phenol with olefin at 70°-40° C. in a fixed bed of an organic sulfonic acid cation exchange resin.

A Lewis acid, Bronsted acid or aluminum chloride catalyst is employed in U.S. Pat. No. 4,096,209 to Ciba-Geigy to prepare a phosphorylated butylated phenol/-phenol ester mixture.

In U.S. Pat. No. 2,684,389 to Gulf R & D a phenol and mono-olefin are mixed in the presence of a silica-aluminum adsorbent catalyst at 137° C. A silica-alumina catalyst is also employed in U.S. Pat. No. 3,876,710 to Hitachi to produce PTBP from phenol and isobutylene.

A $BF_3$ catalyst is used for the reaction of phenol and isobutene in British 1,294,781 to Hoechst where the product cooled to form crystals which are crushed before ammonia is added to remove the catalyst. British 1,249,571 is related.

In German Offen. 3,443,736 to Huels the catalyst is a sulfonated polystyrene ion exchange catalyst. U.S. Pat. No. 4,461,916, also to Huels, discloses a two-stage approach for producing p-tert-octylphenol using an acid ion exchange resin. U.S. Pat. No. 4,236,033 and U.S. Pat. No. 4,168,390 to Huels also disclose ion exchange resins, the latter comprising a LEWATIT ® resin deactivated with $Al_2(SO_4)_3$.

British Patent 2,120,953 to ICI discloses a process for producing nonylphenol by reacting diisobutene with phenol in the presence of a catalyst comprising fuller's earth with alkyl or aryl phosphate or phosphate ester.

U.S. Pat. No. 3,872,173 to Progil discloses the reaction of gaseous isobutene with liquid phenol in the presence of an acid-activated clay, again in two steps.

A highly acidic aryl sulfonic acid catalyst is employed in U.S. Pat. No. 3,932,537 to react phenol with isobutene under anhydrous conditions.

U.S. Pat. No. 3,422,157 to Union Carbide employs a cation exchange resin catalyst.

British Patent 1,314,623 to Union Rheinische Braunkohlen discloses an activated, acid-free bleaching earth catalyst.

In U.S. Pat. No. 4,260,833, to UOP, phenol and isobutylene are reacted at 250° C. in the presence of a lithiated alumina catalyst. U.S. Pat. No. 3,929,912 discloses a more general alkylation of phenol and olefins in the presence of hydrogen fluoride and carbon dioxide.

An aluminum phenoxide catalyst is used for the orthoalkylation of phenol with butene-1 in French Patent 2,296,610, and U.S. Pat. No. 3,766,276, to Ethyl, as well as U.S. Pat. No. 3,933,927.

A boron trifluoride catalyst is used for the alkylation of phenol in U.S. Pat. No. 3,317,612.

Activated earth and phosphoric acid are used in a liquid phase transalkylation process in British Patent 1,444,935.

Acids are also useful for the condensation of phenol with acetone. Representative acids include an aromatic sulfonic acid (German Offen. 2,811,182 and U.S. Pat. No. 4,387,251), a volatile acid catalyst (U.S. Pat. No. 2,623,908), a strong mineral acid such as HCl or $H_2SO_4$ (U.S. Pat. No. 2,359,242), hydrochloric acid (U.S. Pat. No. 4,517,387), $H_2SO_4$ or HCl and 2-(4-pyridyl)ethanethiol (Japanese Kokai-57-118528), concentrated HCl (Japanese Kokai 60-38335) and hydrogen chloride (U.S. Pat. No. 4,169,211).

The use of clays as catalysts for selected applications is known in the art. In an article titled "Catalysis: Selective Developments", Chem. Systems Report 84-3, 239-249, section 3.4320, the unusual properties of smectite clays which make them of interest as catalysts are discussed. These compositions are layered and exhibit a 2:1 relationship between tetrahedral and octahedral sites In addition the combination of cation exchange, intercalation and the fact that the distance between the layers can be adjusted provide interesting possibilities.

An article by F. Figueras, titled "Pillared Clays as Catalysts", in Catal. Rev.-Sci. Eng., 30, 457 (1988) discusses methods of modifying clays and the effects of the modifications. At page 472, there is a discussion of the method of drying, i.e. air drying or freeze drying, which can affect the macroporosity of the resulting product and, as expected, the adsorption capacity. The author concludes the thermal stability of pillared clays can be improved to reach 800° C. using information available with respect to intercalation and drying methods.

Figueras notes, page 481, that the acid strength of montmorillonites was found to be higher than that of Y-zeolites and, in the case of the clays, Bronsted acidity appears to be weaker than Lewis acidity. The author describes three kinds of acid sites known to exist at the surface of clay and suggests the coexistence of several types of acidity makes the localization of acid sites more difficult than in well-crystallized structures.

There is a review of the catalytic activity of pillared clays by T. Matsuda and E. Kikuchi, titled "Acidic Properties of Pillared Clays in Relation to Their Catalytic Behavior", in Proceedings of International Symposium on Acid-Base Catalysis, Sapporo, Nov. 28-Dec. 1, 1988. In Ch. 3.11 these authors observed Bronsted acid sites are responsible for isomerization whereas both Bronsted and Lewis acid sites can catalyze disproportionation. Other pertinent findings were that Bronsted sites are far more active than Lewis sites, however, studies would indicate an irreversible change of Bronsted acidity to Lewis acidity in the course of high temperature calcination, ibid, page 354. They concluded that cracking of a compound such as cumene, for example, depended only on the acidic properties, however disproportion activity was affected by the pore structure in addition to acidity. This was thought to relate to the fact that pillared montmorillonite had regular micropores while pillared saponite consisted of macropores. In addition saponite is tetrahedrally charged clay with Al cations substituting for Si cations. In montmorillonite, in contrast, Mg cations are octahedrally substituted for Al cations At page 352, it is stated that cracking activity is satisfactorily related to Bronsted acidity while it is difficult to find any relationship between the disproportionation activity and the acidic property.

In British Patent GB 1,265,152 ortho-alkylated phenols were prepared in about 52% yield using Fulmont at 300° C. with a small amount of sulfuric acid In German Patent 2,552,175, KSF was the catalyst and about 15% para-product was formed.

There is a review of the use of pillared, cation-exchanged and acid-treated montmorillonite as catalysts for certain organic reactions by J.M. Adams et al., J. Inclusion Phenomena, 5, 663 (1987), Applied Clay Science, 2, 309 (1987). These clays display Bronsted and Lewis acid activities. It is noted that while some cationic species ar stable in solution over a wide concentration and pH range, others are not, particularly solutions containing aluminum. It is noted that it is difficult to ensure a reproducible $Al^{3+}$ clay and moreover, since workers have used slightly different exchanging and washing procedures, a comparison between related experiments is hindered. Commercial acid-treatment is carried out using concentrated hydrochloric, sulphonic or phosphoric acids. The concentration of the acid and the time of the treatment is variable. Sometimes the excess acid is removed by washing, whereas in other products this is not the case. Therefore there is a great variety in the type and activity of acid-treated clays.

Montmorillonites have been used as catalysts for the reaction of straight chain alk-1-enes to ethers, and for alkenes plus alcohols. In the latter, primary alcohols gave high yields, secondary less and tertiary alcohols only trace amounts. The $Al^{+3}$ clays have efficiencies of one third to one half of Amberlyst ® 15 in reactions of this type without solvent or using 1,4-dioxane.

The acid-treated clay K-306 can be used to convert methanol and ammonia to methylamines. Acid-treated clays have also been used to convert cumene hydroperoxide to phenol and acetone.

Of the known processes for producing alkylphenols, generally the processes require two stages for cooling and recycling and many of the catalysts are not stable at high temperatures. In addition, it is often difficult to obtain a high para- to ortho- ratio or to obtain, in the case of nonylphenol synthesis more monononylphenol relative to dinonylphenol and from the art it would appear that conversions of about 80% are about the most which could be expected in any process to prepare alkylphenols.

It would be a distinct advance in the art if alkylphenols such as nonylphenols and particularly para-nonylphenols could be prepared in one step with conversion of nonene as high as 97%. It would be particularly desirable if the catalyst exhibited high thermal stability. Such a process would be especially attractive commercially if the system were operated adiabatic, since close temperature control, cooling and recycling make many processes considerably more expensive.

It is an object of the instant invention to provide a one-step process for the synthesis of alkylphenols in high yield and with almost complete conversion of olefin using a catalyst system which can operate under adiabatic conditions and exhibits stability even at elevated temperatures Another object is to obtain high selectivity while, at the same time, producing a high ratio of para- to ortho- alkylphenol.

SUMMARY OF THE INVENTION

In accordance with the foregoing the novel method of the instant invention for preparing alkylphenols comprises reacting a phenol with the corresponding olefin in the presence of a catalyst comprising an acidic montmorillonite clay treated with an acid selected from the group consisting of hydrogen fluoride, a fluorosulfonic acid or anhydride, and a mineral acid, at temperatures of from about 60° C. to 250° C.

DESCRIPTION OF THE PREFERRED EMBODIMENT

Preparation of the product of this invention may be carried out typically by reacting the phenol and the olefin under adiabatic conditions. The products demonstrate high selectivities and yields. In the examples where the olefin is nonene, the product is made up of a large ratio of the most desirable form of nonlyphenol, para-nonylphenol, compared to ortho-nonlyphenol.

The reaction can be represented by the following:

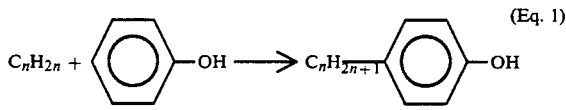
(Eq. 1)

where n is three or greater, preferably in the range 4 to 12.

The olefins which are useful in the instant invention are those which are often available from petrochemical operations. Examples include propylene, 1- and 2-butenes, isobutene and isopentene. Others include isoheptene, diisobutylene, mixed octenes, mixed nonenes, decenes and dodecenes or carbon mixtures thereof. In addition higher straight chain olefins produced by ethylene oligomerization or by dehydrogenation or chlorination-dehydrochlorination of straight chain paraffins are also useful.

Preferred olefins are $C_6$–$C_{12}$ olefins and particularly useful are mixed octenes and mixed nonenes, or mixtures thereof. The examples herein demonstrate the production of p-nonylphenol, which is the preferred form of an important specialty chemical. Nonylphenol is in demand as an intermediate for surfactants, antioxidants and lubricating oil additives.

The molar ratio of the olefin to phenol can vary, but is generally in the ratio of 1:5–5:1. The preferred molar ratio is about 1:1.

As stated the catalyst comprises an inorganic clay which is acid activated and modified with an acid selected from the group consisting of hydrogen fluoride, fluorosulfonic acids and anhydrides, and sulfuric acid plus combinations thereof. Suitable fluorosulfonic acids or anhydrides include fluorosulfonic acid, trifluoromethanesulfonic acid (triflic acid) and trifluoromethanesulfonic anhydride.

The inorganic clays which used to effect this reaction are preferably silica and alumina-rich montmorillonite clay catalysts. A variety of clay catalysts containing alumina and silica are effective in the subject reaction, however it is necessary that the alumina or silica be acidic under normal operating conditions. A group of catalysts which works well in this synthesis are acidic clay mineral catalysts. Chemically clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in the reaction of Equation 1 are smectite clays. Smectite clays are discussed in the article cited in Chem. Systems Report, 84-3. These clays have small particle size and unusual intercalation properties which afford them high surface area. They are alumino silicates with a unique structure that permits modifications and which provide useful catalysts. They comprise layered sheets of octahedral sites between sheets of tetrahedral sites, and the distance between the layers can be adjusted by swelling, through treatment with the appropriate solvent, or treatment with a pillaring or Lewis acid reagent etc. What renders the smectites of particular interest among the clay minerals is their combination of cation exchange, intercalation and swelling properties.

The three-layer sheet types of smectite clays include montmorillonite, vermiculite and certain micas, all of which may be expanded between their layers by the appropriate treatment. The idealized basic structure of clays of this type is that of a pyrophyllite which has the basic formula $Si_8Al_4O_{20}(OH)_4$.

A general representation of the montmorillonite structure is:

$$M_{x/n}{}^{n+} \cdot yH_2O(Al_{4-x}Mg_x)(Si_8)O_{20}(OH)_4$$

where M represents the interlamellar (balancing cation, normally sodium or lithium) and x, y and n are integers.

These montmorillonite clays are best used in the present application in an acidic form. Acids activate montmorillonites by attacking and solubilizing structural cations in the octahedral layers. This opens up the clay structure and increases surface area. These acid-treated clays act as strong Bronsted acids. Generally strong mineral acids are used to activate the clay, such as, for example, sulfuric acid and phosphoric acid. As noted in the Matsuda reference, supra, there is an indication Bronsted sites are more active, but have a tendency to convert to Lewis acid sites as temperature increases during calcination of pillared clays. The clays are effective in the form of granules, powders or extrudates.

The acid-treated montmorillonite clays of the present invention upon which the triflic acid or hydrofluoric acid are deposited should have acidities of 1.0 or greater mg KOH/gm, and preferably 5 to 100 mg KOH/gm, titrated to a phenolphthalein end point. Their surface area should be $\geq 30$ m$^2$/g, and preferably 200 to 1000 m$^2$/g. Their moisture content should be limited also, whereby upon heating to 220° F., the weight loss is generally less than 20 wt %, but may be higher under certain circumstances.

Illustrative examples of suitable acidic montmorillonite clays include clays in granular form, such as Filtrol grade 24, having a 20–60 mesh size, and Grade 24 Superacid Clay. Filtrol grade 24 is manufactured by Engelhard and has an acid capacity of 25 mg KOH/g. Grade 24 Superacid Clay, also from Engelhard, has an acidity of 33 mg KOH/g.

Where the montmorillonite clay or acid-pretreated montmorillonite clay, as described above, is impregnated with triflic acid or hydrogen fluoride, the clay is generally treated with from 0.01% to 10% triflic acid or HF and preferably the clay is impregnated with from about 0.1% to 1.0% triflic acid. The instant examples demonstrate that about 0.1% to 1.0% is an effective amount.

Where hydrogen fluoride is deposited on acidic montmorillonite about 0.1% to 1.0% is a preferred effective amount.

An effective amount of triflic acid would be sufficient to produce an acidity of the catalyst in the range of 1-100 mg KOH/g. An effective amount of hydrogen fluoride would be sufficient to produce a catalyst acidity in the range of 1 to 100 mg KOH/g.

Preparation of alkylphenols is conducted in a fixed bed, continuous flow reactor.

The reaction is conducted under adiabatic conditions. The "hot spot" or maximum temperature of the reactor can be in the range of 60°–250° C. and preferably 80° C. to 140° C. The preferred temperature depends on the choice of reactants, however, in the case of nonene and phenol an effective temperature is about 90° C. The pressure can be in the range of atmospheric to 500 psi and is preferably about 100 psi.

Typically the alkylphenol is generated continuously in up to ca. 80+ wt % concentration in the crude product liquid effluent.

Olefin conversions are high. Nonenes conversion is almost quantitative, as high as 97%. Preferably the nonenes conversion is >90% and the para-nonylphenol to ortho-nonylphenol weight ratio is >5.

These yields are achieved at a total liquid hourly space velocity (LHSV) of one to 10 under mild conditions.

Here LHSV is defined as follows:

$$LHSV = \frac{\text{Weight of Total Liquid Feed Run Through the Reactor Per Hour}}{\text{Volume of Catalyst in Reactor}}$$

Conversion of olefins (wt %) is estimated in the following examples using the equation:

$$100 - \left( \frac{\text{Wt \% Conc. of Olefin in Product}}{\text{Wt \% Conc. of Olefin in Feed}} \right) \times 100$$

Yields of alkylphenol (mole %) are estimated from:

$$\frac{\text{Moles of Alkylphenyl in Product Liquid}}{\text{Moles of Olefin in Feed}} \times 100$$

The accompanying examples illustrate:
1. In Example 1, using the 0.5% HF-treated clay catalyst, run adiabatically:
   a) 97% nonenes conversion per pass at 100° C., LHSV 1,
   b) p-nonylphenol to o-nonylphenol ratio of 13.5 at 80° C. with nonylphenol to dinonylphenol ratio of 9.0 at 80° C., and
   c) 79% nonenes conversion per pass at 100° C., LHSV 3.
2. In Examples 2–5, other acid-treated clays likewise give good-performances. For example, in the case of the 0.1% triflic clay catalyst (Example 3) and the sulfuric acid-treated clays (Examples 2, 4 and 5), the calculated nonene conversions, nonylphenol total concentration and para-to-ortho nonylphenol ratios, as well as the nonylphenol to dinonylphenol ratios, are summarized in Table 6. In all cases these acid-treated clays give:

a) High nonene conversions per pass;
b) High total nonylphenol concentrations in the crude product effluent;
c) High p-nonylphenol to o-nonylphenol ratios;
d) High total nonylphenol to dinonylphenol ratios; and
e) Good performance at higher LHSV's.

Product analyses were primarily by gas liquid chromatography (glc) and liquid chromatography (lc).

The examples which follow illustrate the generation of alkylphenols from phenol and the corresponding olefin using acidic montmorillonite clays modified with specified acids. These examples are only intended as a means of illustration and it should be understood the invention is not meant to be limited thereby.

EXAMPLE 1

This example illustrates the selective production of para-nonylphenol from phenol and mixed nonenes using a hydrofluoric acid-treated montmorillonite clay catalyst.

Synthesis was conducted in a 500 cc capacity, tubular reactor constructed of stainless steel, operated upflow and fitted with temperature, pressure and flow rate regulating devices.

The reactor was charged at the beginning of the experiment with 400 cc of 0.5% hydrogen fluoride on montmorillonite clay that had previously been treated with sulfuric acid, as granules, having an acid capacity of 25 mg KOH/g and a water content of 18.4%. A screen of glass wool was placed at the top and bottom of the reactor to ensure the catalyst would remain in the middle portion.

Said catalyst bed was treated with a phenol/nonene mix (1:1 weight mix, 1.34:1 molar ratio) upflow, at a rate of 400 cc/hr, while the first section of the catalyst bed was held at 80° C. The reactor was run adiabatically and the hot spot temperature along the catalyst bed was at least 100° C.; total pressure was 100 psi. Samples of crude product effluent were collected after the unit had reached steady-state conditions and analyzed by glc and lc typical analyses data are given in Table 1.

The experiment was repeated at a series of set-point temperatures (100°, 120° C.) and flow rates (800, 1200 cc/hr) under adiabatic conditions. These run and results data are also given in Table 1.

TABLE 1
NONYLPHENOL SYNTHESIS

| Ex. | Catalyst | PhOH/$C_9^-$ Molar Ratio | Control Temp. (°C.) | Feed Rate (cc/hr) | Sample | $C_9^-$ | PhOH | NP | DNP | DNP | o-NP | p-NP | Hot Spot Temp (°C.) |
|---|---|---|---|---|---|---|---|---|---|---|---|---|---|
|   |   |   |   |   |   |   | glc |   |   |   | lc |   |   |
| 1 | 0.5% HF on Clay | 1.34 |   |   | FS-1 | 50.6 | 49.4 |   |   |   |   |   |   |
|   |   |   | 80 | 400 | 1 | 2.9 | 18.2 | 70.9 | 7.9 | 5.8 | 6.3 | 84.9 | 102 |
|   |   |   | 100 | 400 | 2 | 1.7 | 16.8 | 73.3 | 7.7 | 6.2 | 7.3 | 85.2 | 117 |
|   |   |   | 120 | 400 | 3 | 3.1 | 18.5 | 66.9 | 11.1 | 9.8 | 12.4 | 75.4 | 156 |
|   |   |   | 100 | 800 | 4 | 6.4 | 20.2 | 66.3 | 7.0 | 5.5 | 6.6 | 84.2 | 110 |
|   |   |   | 100 | 1200 | 5 | 10.7 | 22.7 | 60.5 | 6.0 | 5.2 | 6.6 | 83.7 | 119 |

$^a C_9^-$, Mixed Nonenes. PhOH, Phenol; NP, Nonylphenols; DNP, Dinonylphenols; o-NP, Ortho-Nonylphenols; p-NP, Para-Nonylphenols

EXAMPLES 2–=

These examples illustrate the selective production of para-nonylphenol from phenol and mixed nonenes using a variety of other acid-treated montmorillonite clay catalysts.

Following the procedures of Example 1, a series of acid-treated montmorillonite clays were used as catalysts with phenol/nonene feed mix (1:34:1 molar ratio) under adiabatic operating conditions, at a series of operating temperatures (80°–20° C.) and feed rates (400–200 cc/hr). The catalysts tested comprised:
a) A sulfuric acid-treated clay having an acidity of 33 mg KOH/g.
b) A triflic acid-(TF)-treated clay having an acidity of 11 mg KOH/g and a water content of 17.2%.
c) Another sulfuric acid-treated clay having an acidity of 93 mg KOH/g.
d) A further sample of sulfuric acid-treated clay having an acidity of 5 mg KOH/g and a water content of <1%.

Run data and results are summarized in Tables 2–5.

TABLE 2
NONYLPHENOL SYNTHESIS

| Ex. | Catalyst | PhOH/$C_9^-$ Molar Ratio | Control Temp. (°C.) | Feed Rate (cc/hr) | Sample | $C_9^-$ | PhOH | NP | DNP | DNP | o-NP | p-NP | Hot Spot Temp (°C.) |
|---|---|---|---|---|---|---|---|---|---|---|---|---|---|
|   |   |   |   |   |   |   | glc |   |   |   | lc |   |   |
| 2 | $H_2SO_4$ Treated Clay$^a$ | 1.34 |   |   | FS-1 | 50.9 | 49.1 |   |   |   |   |   |   |
|   |   |   | 80 | 400 | 1 | 4.0 | 19.1 | 68.9 | 7.9 | 6.5 | 6.3 | 84.2 | 100 |

TABLE 2-continued

NONYLPHENOL SYNTHESIS

| Ex. | Catalyst | PhOH/C$_9^-$ Molar Ratio | Control Temp. (°C.) | Feed Rate (cc/hr) | Sample | PRODUCT COMPOSITION (%)$^a$ glc C$_9^-$ | PhOH | NP | DNP | lc DNP | o-NP | p-NP | Hot Spot Temp (°C.) |
|---|---|---|---|---|---|---|---|---|---|---|---|---|---|
| | | | 100 | 400 | 2 | 1.8 | 17.6 | 72.3 | 8.0 | 6.6 | 7.0 | 82.5 | 107 |
| | | | | | FS-2 | 50.4 | 49.4 | | | | | | |
| | | | 120 | 400 | 3 | 2.6 | 19.6 | 65.4 | 12.5 | 12.5 | 13.9 | 69.9 | 132 |
| | | | 100 | 800 | 4 | 3.4 | 19.7 | 64.8 | 11.4 | 12.1 | 14.4 | 68.8 | 165 |
| | | | 100 | 1200 | 5 | 7 | 23.7 | 56.1 | 10.4 | 11.3 | 22.6 | 48.0 | 200 |

$^a$Acidity, 33 mg KOH/g

TABLE 3

NONYLPHENOL SYNTHESIS

| Ex. | Catalyst | PhOH/C$_9^-$ Molar Ratio | Control Temp. (°C.) | Feed Rate (cc/hr) | Sample | PRODUCT COMPOSITION (%)$^a$ glc C$_9^-$ | PhOH | NP | DNP | lc DNP | o-NP | p-NP | Hot Spot Temp (°C.) |
|---|---|---|---|---|---|---|---|---|---|---|---|---|---|
| 3 | TF Treated Clay$^a$ | 1.34 | | | FS-1 | 50.5 | 49.5 | | | | | | |
| | | | 80 | 400 | 1 | 3.0 | 18.8 | 69.2 | 8.2 | 6.2 | 6.4 | 84.2 | 104 |
| | | | 100 | 400 | 2 | 2.7 | 18.0 | 70.7 | 7.7 | 5.9 | 6.9 | 84.6 | 118 |
| | | | 120 | 400 | 3 | 2.3 | 17.9 | 70.4 | 8.6 | 6.9 | 8.9 | 82.3 | 130 |
| | | | 100 | 800 | 4 | 3.9 | 19.3 | 67.4 | 8.5 | 8.8 | 10.1 | 77.7 | 143 |
| | | | 100 | 1200 | 5 | 5.6 | 20.0 | 63.2 | 8.8 | 8.0 | 13.7 | 75.5 | 170 |

$^a$Acidity, 11 mg KOH/g

TABLE 4

NONYLPHENOL SYNTHESIS

| Ex. | Catalyst | Temp. (°C.) | Feed Rate (cc/hr) | Sample | PRODUCT COMPOSITION (%)$^a$ glc C$_9^-$ | PhOH | NP | DNP | lc DNP | o-NP | p-NP | Hot Spot Temp (°C.) |
|---|---|---|---|---|---|---|---|---|---|---|---|---|
| 4 | H$_2$SO$_4$ Treated Clay$^a$ | | | FS-1 | 49.9 | 50.1 | | | | | | |
| | | 80 | 400 | 1 | 10.6 | 23.4 | 59.3 | 6.6 | 10.7 | 4.4 | 81.2 | 92 |
| | | 100 | 400 | 2 | 2.9 | 18.3 | 70.0 | 8.2 | 11.8 | 5.6 | 80.8 | 119 |
| | | 120 | 400 | 3 | 3.2 | 19.3 | 65.6 | 11.1 | 16.2 | 9.3 | 71.9 | 135 |
| | | 100 | 800 | 4 | 6.5 | 20.9 | 64.9 | 7.3 | 10.8 | 5.9 | 80.7 | 132 |
| | | 100 | 1200 | 5 | 7.0 | 22.1 | 62.5 | 7.8 | 12.9 | 9.3 | 74.9 | 157 |

$^a$Acidity, 93 mg KOH/g

TABLE 5

NONYLPHENOL SYNTHESIS

| Ex. | Catalyst | PhOH/C$_9^-$ Molar Ratio | Control Temp. (°C.) | Feed Rate (cc/hr) | Sample | PRODUCT COMPOSITION (%)$^a$ glc C$_9^-$ | PhOH | NP | DNP | lc DNP | o-NP | p-NP | Hot Spot Temp (°C.) |
|---|---|---|---|---|---|---|---|---|---|---|---|---|---|
| 5 | H$_2$SO$_4$ Treated Clay$^a$ | 1.34 | | | FS-1 | | | | | | | | |
| | | | 80 | 400 | 1 | 17.4 | 30.2 | 44.3 | 8.0 | 17.7 | 5.3 | 74.2 | 84 |
| | | | 100 | 400 | 2 | 10.5 | 25.0 | 55.6 | 8.4 | 14.0 | 4.8 | 77.8 | 109 |
| | | | 120 | 400 | 3 | 6.1 | 21.5 | 63.7 | 8.3 | 12.1 | 5.0 | 79.9 | 127 |
| | | | 100 | 800 | 4 | 12.4 | 26.1 | 53.5 | 7.5 | 13.7 | 5.0 | 77.9 | 129 |
| | | | 100 | 1200 | 5 | 13.0 | 26.5 | 53.1 | 6.9 | 12.5 | 5.5 | 78.5 | 142 |

$^a$Acidity, 5 mg KOH/g

TABLE 6

NONYLPHENOL PRODUCT ANALYSES DATA

| Ex. | Catalyst | Sample | Set Point Temp. (°C.) | LHSV | Nonene Conv (%) | NP Conc (%) | Weight Ratio p-NP/o-NP | NP/DNP |
|---|---|---|---|---|---|---|---|---|
| 1 | 0.5% HF/Clay | 1 | 80 | 1 | 94 | 71 | 13.5 | 9.0 |
| | | 3 | 120 | 1 | 94 | 67 | 6.1 | 6.0 |
| | | 5 | 100 | 3 | 79 | 61 | 12.7 | 10.1 |
| 2 | H$_2$SO$_4$/Clay | 1 | 80 | 1 | 92 | 69 | 13.4 | 8.7 |
| | | 3 | 120 | 1 | 96 | 65 | 5.0 | 5.4 |
| | | 5 | 100 | 3 | 84 | 56 | 2.1 | 5.4 |
| 3 | 0.1% TF/Clay | 1 | 80 | 1 | 94 | 69 | 13.2 | 8.4 |
| | | 3 | 120 | 1 | 95 | 70 | 9.2 | 8.2 |
| | | 5 | 100 | 3 | 89 | 63 | 5.5 | 7.2 |
| 4 | H$_2$SO$_4$/Clay | 1 | 80 | 1 | 79 | 59 | 18.5 | 9.0 |

TABLE 6-continued

NONYLPHENOL PRODUCT ANALYSES DATA

| Ex. | Catalyst | Sample | Set Point Temp. (°C.) | LHSV | Nonene Conv (%) | NP Conc (%) | Weight Ratio p-NP/o-NP | NP/DNP |
|---|---|---|---|---|---|---|---|---|
|  |  | 3 | 120 | 1 | 94 | 66 | 7.7 | 5.9 |
|  |  | 5 | 100 | 3 | 86 | 63 | 8.1 | 8.0 |
| 5 | H$_2$SO$_4$/Clay | 1 | 80 | 1 | 67 | 44 | 14.0 | 5.5 |
|  |  | 3 | 120 | 1 | 88 | 64 | 16.0 | 7.7 |
|  |  | 5 | 100 | 3 | 75 | 53 | 14.3 | 7.7 |

What is claimed is:

1. A one step method for synthesis of alkylphenols which comprises reacting phenol with the corresponding olefin under adiabatic conditions in the presence of a catalyst comprising montmorillonite clay at a temperature of from 60° C. to 250° C. and a pressure of near atmospheric to about 500 psi, wherein the clay is acidic from pretreatment with an acid selected from the group comprising hydrogen fluoride, fluorosulfonic acids or anhydrides, or mineral acids, as well as combinations thereof.

2. The method of claim 1 wherein the olefin is selected from the group consisting of mixed octenes, mixed nonenes, mixed dodecenes and mixtures thereof.

3. The method of claim 1 wherein the olefin is mixed nonenes and the alkylphenols are nonylphenols.

4. The method of claim 2 wherein the mineral acid used to acid activate the clay is sulfuric acid.

5. The method of claim 4 wherein the montmorillonite clay is treated with sulfuric acid and has an acidity of 1.0 or greater mg KOH/gm.

6. The method of claim 4 wherein the montmorillonite clay is treated with hydrogen fluoride.

7. The method of claim 4 wherein the acidity of the sulfuric acid-treated clay is in the range of 5-100 mg KOH/g.

8. The method of claim 4 wherein the sulfuric acid-treated montmorillonite clay has deposited thereon 0.1% to 10% wt % hydrogen fluoride.

9. The method of claim 4 wherein the sulfuric acid-treated montmorillonite clay has deposited thereon 0.5% by weight hydrogen fluoride.

10. The method of claim 8 wherein the acidity of the hydrogen fluoride treated clay is in the range of 1 to 100 mg KOH/g.

11. The method of claim 1 wherein the fluorosulfonic acid is selected from the group comprising fluorosulfonic acid and triflic acid.

12. The method of claim 11 wherein the montmorillonite clay has deposited thereon 0.1% to 10% wt % triflic acid.

13. The method of claim 11 wherein the montmorillonite clay has deposited thereon 0.1% by weight triflic acid.

14. The method of claim 11 wherein the acidity of the triflic acid-treated clay is in the range of 2-15 mg KOH/g.

15. The method of claim 1 wherein the fluorosulfonic anhydride is trifluoromethanesulfonic anhydride.

16. The method of claim 1 wherein the maximum operating temperature is in the range of 80° to 140° C.

17. The method of claim 3 wherein the nonenes to phenol molar feed ratio is 1:5 to 5:1.

18. The method of claim 17 wherein the nonenes conversion is >90% and the para-nonylphenol to ortho-nonylphenol weight ratio is >5.

* * * * *